(12) United States Patent
Elhadad et al.

(10) Patent No.: US 7,347,841 B2
(45) Date of Patent: Mar. 25, 2008

(54) PROTECTOR FOR ADMINISTERING MEDICINE

(76) Inventors: Yisrael Elhadad, 16/8 Ido HaNavi St., Jerusalem 95106 (IL); Yisrael Gottlieb, f/ Miriam Mizrahi St., Rehovot 76100 (IL)

( * ) Notice: Subject to any disclaimer, the term of this patent is extended or adjusted under 35 U.S.C. 154(b) by 451 days.

(21) Appl. No.: 10/990,502

(22) Filed: Nov. 18, 2004

(65) Prior Publication Data

US 2006/0102503 A1  May 18, 2006

(51) Int. Cl.
 *A61M 3/00* (2006.01)
(52) U.S. Cl. ...................................... 604/189
(58) Field of Classification Search ............... 604/218, 604/192, 198, 110, 263, 117, 197, 241, 189; 606/1, 108
See application file for complete search history.

(56) References Cited

U.S. PATENT DOCUMENTS

| | | | | |
|---|---|---|---|---|
| 4,415,802 A | * | 11/1983 | Long | 235/382 |
| 4,438,845 A | * | 3/1984 | Mochow | 206/366 |
| 5,272,318 A | * | 12/1993 | Gorman | 235/375 |
| 5,507,277 A | * | 4/1996 | Rubsamen et al. | 128/200.14 |
| 6,368,305 B1 | * | 4/2002 | Dutton | 604/192 |

* cited by examiner

*Primary Examiner*—Manuel Mendez
(74) *Attorney, Agent, or Firm*—Deket Patent Ltd.; David Klein

(57) ABSTRACT

A medicine assembly, and a protector that fits over at least a portion of the medicine assembly, the protector including a bar code and a locking element openable by means of a bar code reader reading the bar code, wherein when the locking element is in a locked orientation, the protector substantially prevents administration of a substance from the medicine assembly.

10 Claims, 1 Drawing Sheet

PROTECTOR FOR ADMINISTERING MEDICINE

FIELD OF THE INVENTION

The present invention relates generally to assemblies for administering medicine and particularly to a device that prevents unauthorized use of a medicine assembly (e.g., needle assembly and others), such as to prevent unauthorized administration of a drug or medicinal substance.

BACKGROUND OF THE INVENTION

Hypodermic needle assemblies are commonly used to administer drugs or other medicinal substances, whether in a hospital or clinic or at home. Sometimes the hypodermic needle assembly is prepared ahead of time and stored in a cabinet or refrigerator until use. For example, a medical practitioner (e.g., a nurse) may have instructions for administering a certain medicine hypodermically to a certain patient. The medical practitioner may inadvertently take the incorrect needle assembly from the cabinet or refrigerator and administer the wrong medicine to that particular patient, with possibly serious repercussions. It would therefore be desirable to prevent unauthorized administration of a drug or medicinal substance from a hypodermic needle assembly and the like.

SUMMARY OF THE INVENTION

The present invention seeks to provide a protector for a medicine assembly, which prevents unauthorized administration of a drug or medicinal substance, as is described more in detail hereinbelow.

There is provided in accordance with an embodiment of the present invention apparatus including a medicine assembly, and a protector that fits over at least a portion of the medicine assembly, the protector including a bar code and a locking element openable by means of a bar code reader reading the bar code, wherein when the locking element is in a locked orientation, the protector substantially prevents administration of a substance from the medicine assembly. For example, the protector may fit over a needle or a plunger of the medicine assembly. The medicine assembly is not limited to needle assemblies, and may include any assembly for storing any kind of medicine (oral, transdermal, rectal, intravenous and others).

In accordance with an embodiment of the present invention, the locking element is electrically operated, wherein upon reading of the bar code, an electrical signal is generated that opens the locking element. The protector may include a plurality of members selectively lockable to one another by means of the locking element, wherein as long as the locking element is in a locked orientation, the members cannot be separated.

BRIEF DESCRIPTION OF THE DRAWINGS

The present invention will be understood and appreciated more fully from the following detailed description taken in conjunction with the drawings in which.

DETAILED DESCRIPTION OF EMBODIMENTS

Figure 1:
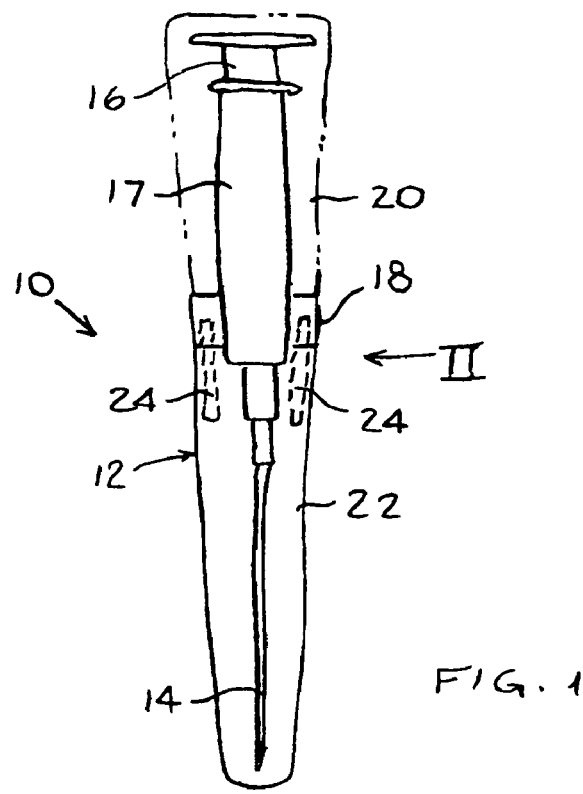
FIG. 1 is a simplified pictorial illustration of a protector for a medicine assembly, constructed and operative in accordance with an embodiment of the present invention.
Figure 2:
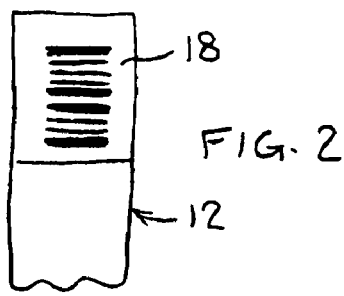
FIG. 2 is a more detailed illustration of a portion of the protector of FIG. 1, showing a bar code that enables deployment of the medicine assembly.
Figure 3:
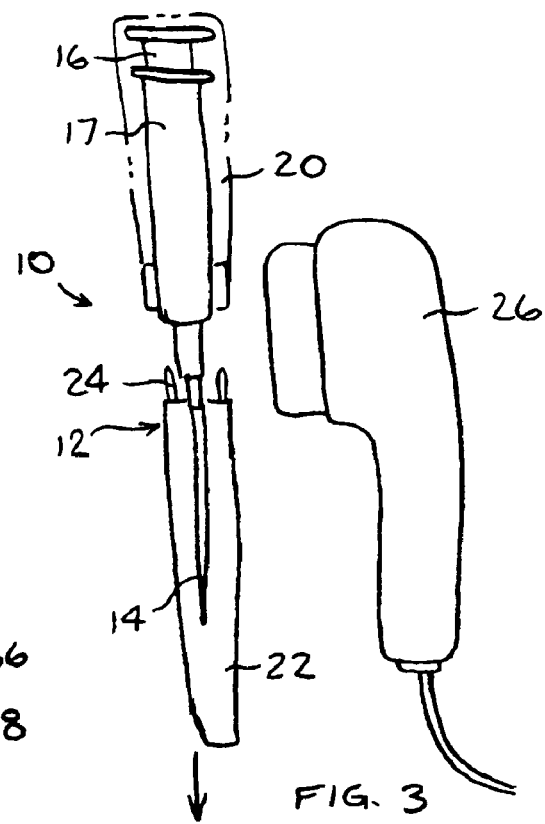
FIG. 3 is a simplified pictorial illustration of using a bar code reader to read the bar code, thereby permitting removal of the protector from the medicine assembly, in accordance with an embodiment of the present invention.

Reference is now made to FIGS. 1-3, which illustrate a medicine assembly 10, constructed and operative in accordance with an embodiment of the present invention. The embodiment illustrated in FIGS. 1-3 is a hypodermic needle assembly, but the invention is not limited to hypodermic needles and may be carried out with jet injection devices or other kinds of injection devices.

A protector 12 is provided that fits over at least a portion of medicine assembly 10. For example, protector 12 may fit over a needle 14 of medicine assembly 10. Alternatively or additionally, protector 12 may fit over a plunger 16 of a syringe 17 of medicine assembly 10.

A bar code 18 (seen best in FIG. 2) may be printed on any suitable portion of protector 12. The term "bar code", throughout the specification and claims, refers not just to a bar code, but rather to any optically or machine readable code or character, such as but not limited to, a magnetic strip or computer-recognizable code.

Protector 12 may include an upper member 20 and a lower member 22, selectively lockable to one another by means of a locking element 24. Locking element 24 may include, without limitation, an electrically operated element, such as a solenoid, or alternatively, a mechanically-operated, hydraulically-operated or pneumatically-operated locking element or any combination thereof. As long as the locking element 24 is in a locked orientation, the upper member 20 and lower member 22 cannot be separated, so that protector 12 substantially prevents administration of a substance from medicine assembly 10.

A bar code reader 26 (FIG. 3) may be used to read the bar code 18. In one non-limiting embodiment of the invention, bar code reader 26 reads the bar code 18 and causes generation of an electrical signal that opens locking element 24. The electrical signal may be generated by a switch, solenoid or other apparatus (not shown), which is in electrical communication with locking element 24.

In accordance with the present invention, the bar code 18 may be specific to a certain patient and certain medicine. A medical practitioner may use the bar code reader 26 to read the bar code 18 prior to using medicine assembly 10. The locking element 24 will open if and only if the bar code read by the bar code reader 26 is associated with the correct patient and medicine. Thus the present invention assures proper administration of medicine to the correct patient.

Figure 4:
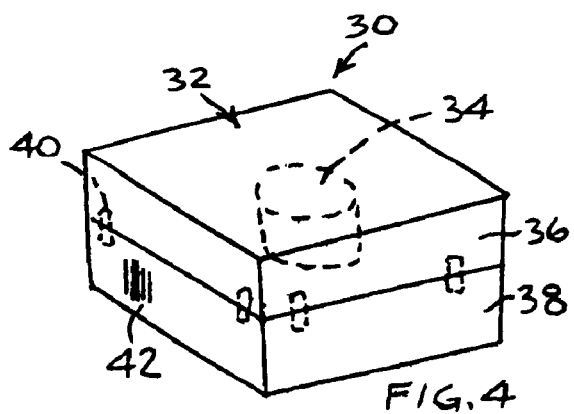
FIG. 4 is a simplified illustration of a medicine assembly, constructed and operative in accordance with another embodiment of the present invention.

Reference is now made to FIG. 4, which illustrates a medicine assembly 30, constructed and operative in accordance with another embodiment of the present invention.

A protector 32 is provided that fits over at least a portion of medicine assembly 30. For example, protector 32 may include an enclosure that surrounds a container 34 of medicine, for oral intake, transdermal delivery or any other kind of medicinal administration. Protector 32 may include two or more members 36 and 38, selectively lockable to one another by means of a locking element 40. Locking element 40 may include, without limitation, an electrically operated element, such as a solenoid, or alternatively, a mechanically-operated, hydraulically-operated or pneumatically-operated locking element or any combination thereof. As long as the locking element 40 is in a locked orientation, the two members 36 and 38 cannot be separated, so that protector 32 substantially prevents administration of the medicine from medicine assembly 30.

A bar code 42 may be printed on any suitable portion of protector 32. Bar code reader 26 (FIG. 3) may be used to read the bar code 42 to open locking element 40, as described hereinabove, and assure proper administration of medicine to the correct patient.

It will be appreciated by persons skilled in the art that the present invention is not limited by what has been particularly shown and described hereinabove. Rather the scope of the present invention includes both combinations and sub-combinations of the features described hereinabove as well as modifications and variations thereof which would occur to a person of skill in the art upon reading the foregoing description and which are not in the prior art.

What is claimed is:

1. Apparatus comprising:
a protector adapted to fit over at least a portion of a medicine assembly, said medicine assembly comprising a correct medicine uniquely intended for administrating to a correct patient, said protector comprising a bar code associated both with the correct patient and the correct medicine and a locking element openable by means of a bar code reader reading said bar code, wherein when said locking element is in a locked orientation, said protector substantially prevents administration of a substance from said medicine assembly, wherein said locking element will open if and only if the bar code read by the bar code reader is associated both with the correct patient and the correct medicine.

2. The apparatus according to claim 1, wherein said protector is adapted to fit over a needle of a medicine assembly.

3. The apparatus according to claim 1, wherein said protector is adapted to fit over a plunger of a medicine assembly.

4. The apparatus according to claim 1, wherein said locking element is electrically operated, wherein upon reading of said bar code, an electrical signal is generated that opens said locking element.

5. The apparatus according to claim 1, wherein said protector comprises a plurality of members selectively lockable to one another by means of said locking element, wherein as long as said locking element is in a locked orientation, said members cannot be separated.

6. Apparatus comprising:
a medicine assembly comprising a correct medicine uniquely intended for administrating to a correct patient; and
a protector that fits over at least a portion of said medicine assembly, said protector comprising a bar code associated both with the correct patient and the correct medicine and a locking element openable by means of a bar code reader reading said bar code, wherein when said locking element is in a locked orientation, said protector substantially prevents administration of a substance from said medicine assembly, wherein said locking element will open if and only if the bar code read by the bar code reader is associated both with the correct patient and the correct medicine.

7. The apparatus according to claim 6, wherein said protector fits over a needle of said medicine assembly.

8. The apparatus according to claim 6, wherein said protector fits over a plunger of said medicine assembly.

9. The apparatus according to claim 6, wherein said locking element is electrically operated, wherein upon reading of said bar code, an electrical signal is generated that opens said locking element.

10. The apparatus according to claim 6, wherein said protector comprises a plurality of members selectively lockable to one another by means of said locking element, wherein as long as said locking element is in a locked orientation, said members cannot be separated.

* * * * *

UNITED STATES PATENT AND TRADEMARK OFFICE
CERTIFICATE OF CORRECTION

PATENT NO. : 7,347,841 B2  Page 1 of 1
APPLICATION NO. : 10/990502
DATED : March 25, 2008
INVENTOR(S) : Israel Elhadad and Israel Gottlieb It is certified that error appears in the above-identified patent and that said Letters Patent is hereby corrected as shown below:

On the title page item (76),
The name and address of Yisrael Elhadad should be corrected to:
Israel Elhadad
42 Northumberland Street
Broughton Green
Salford M74 DG
UK The name of Yisrael Gottlieb should be corrected to:
Israel Gottlieb Signed and Sealed this Nineteenth Day of October, 2010

David J. Kappos
*Director of the United States Patent and Trademark Office*